United States Patent [19]
Alesi et al.

[11] Patent Number: 5,474,566
[45] Date of Patent: Dec. 12, 1995

[54] SELF-CONTAINED POWERED SURGICAL APPARATUS

[75] Inventors: Thomas W. Alesi, New Fairfield, Conn.; Wayne P. Young, Brewster, N.Y.; Henry Bolanos, East Norwalk, Conn.; Carlo A. Mililli, Huntington, Conn.; Dominick L. Mastri, Bridgeport, Conn.; Leonard Stern, Southington, Conn.

[73] Assignee: United States Surgical Corporation, Norwalk, Conn.

[21] Appl. No.: 238,565

[22] Filed: May 5, 1994

[51] Int. Cl.[6] ................................................ A61B 17/00
[52] U.S. Cl. ........................ 606/139; 606/205; 606/143
[58] Field of Search ........................... 606/139, 142, 606/143, 158; 227/902, 175–182

[56] References Cited

U.S. PATENT DOCUMENTS

| | | |
|---|---|---|
| 1,881,250 | 10/1932 | Tomlinson . |
| 3,952,748 | 4/1976 | Kaliher et al. . |
| 4,071,029 | 1/1978 | Richmond et al. . |
| 4,289,131 | 9/1981 | Mueller . |
| 4,334,539 | 6/1982 | Childs et al. . |
| 4,484,503 | 11/1984 | Sitte et al. . |
| 4,489,724 | 12/1984 | Arnegger . |
| 4,494,057 | 1/1985 | Hotta . |
| 4,509,518 | 4/1985 | McGarry et al. . |
| 4,598,711 | 7/1986 | Deniega ................................. 606/143 |
| 4,616,650 | 10/1986 | Green et al. . |
| 4,624,254 | 11/1986 | McGarry et al. . |
| 4,644,952 | 2/1987 | Patipa et al. . |
| 4,650,460 | 3/1987 | Roizenblatt . |
| 4,655,673 | 4/1987 | Hawkes . |
| 4,662,373 | 5/1987 | Montgomery et al. . |
| 4,674,504 | 6/1987 | Klieman et al. . |
| 4,705,038 | 11/1987 | Sjostrom et al. . |
| 4,712,549 | 12/1987 | Peters et al. ............................ 606/143 |
| 4,733,118 | 3/1988 | Mihalko . |
| 4,771,774 | 9/1988 | Simpson et al. . |
| 4,887,599 | 12/1989 | Muller . |
| 4,936,845 | 6/1990 | Stevens . |
| 4,995,877 | 2/1991 | Ams et al. . |
| 5,030,226 | 7/1991 | Green et al. . |
| 5,047,038 | 9/1991 | Peters et al. . |
| 5,049,152 | 9/1991 | Simon et al. ........................ 606/139 X |
| 5,059,203 | 10/1991 | Husted . |
| 5,084,057 | 1/1992 | Green et al. . |
| 5,100,420 | 3/1992 | Green et al. . |
| 5,133,359 | 7/1992 | Kedem . |
| 5,133,713 | 7/1992 | Huang et al. . |
| 5,133,729 | 7/1992 | Sjostrom . |
| 5,171,247 | 12/1992 | Hughett et al. ..................... 606/143 X |
| 5,192,292 | 3/1993 | Cezana et al. . |
| 5,197,970 | 3/1993 | Green et al. ........................ 606/139 X |
| 5,201,750 | 4/1993 | Hocherl et al. . |
| 5,207,697 | 5/1993 | Carusillo et al. . |
| 5,221,279 | 6/1993 | Cook et al. . |
| 5,237,884 | 8/1993 | Seto . |
| 5,249,583 | 10/1993 | Mallaby . |
| 5,258,007 | 11/1993 | Spetzler et al. ..................... 606/139 X |
| 5,261,877 | 11/1993 | Fine et al. . |
| 5,268,622 | 12/1993 | Philipp . |
| 5,300,081 | 4/1994 | Young et al. . |

FOREIGN PATENT DOCUMENTS

| | | |
|---|---|---|
| 552050 | 7/1993 | European Pat. Off. ........... 606/143 X |
| 0598529 | 5/1994 | European Pat. Off. . |
| 0634144 | 1/1995 | European Pat. Off. . |
| 9308754 | 5/1993 | WIPO . |
| 9314706 | 8/1993 | WIPO . |

*Primary Examiner*—Peter A. Aschenbrenner

[57] ABSTRACT

A self-contained powered surgical clip applier is provided which includes an elongate body defining a longitudinal axis and housing a plurality of surgical clips. The powered clip applier further includes a jaw assembly operatively associated with a distal end of the elongate body and actuable to move between an open position and a closed position, a motor assembly disposed within the elongate body, a power supply positioned within the elongate body for energizing the motor assembly, a clip pusher configured to individually advance surgical clips into the jaw assembly, and an actuation channel driven by the motor assembly and configured to translate through the elongate body to drive the clip pusher and actuate the jaw assembly.

33 Claims, 11 Drawing Sheets

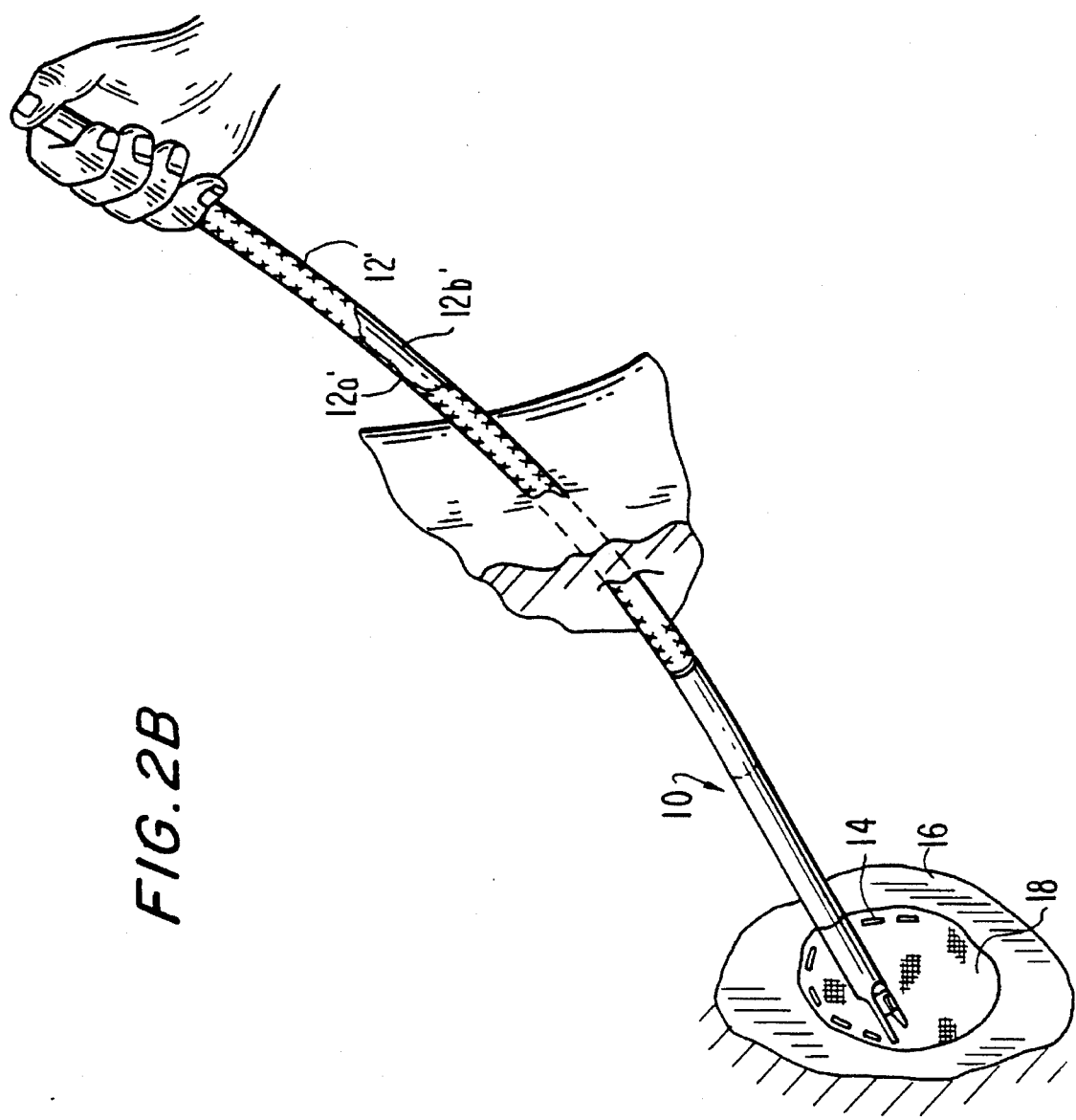

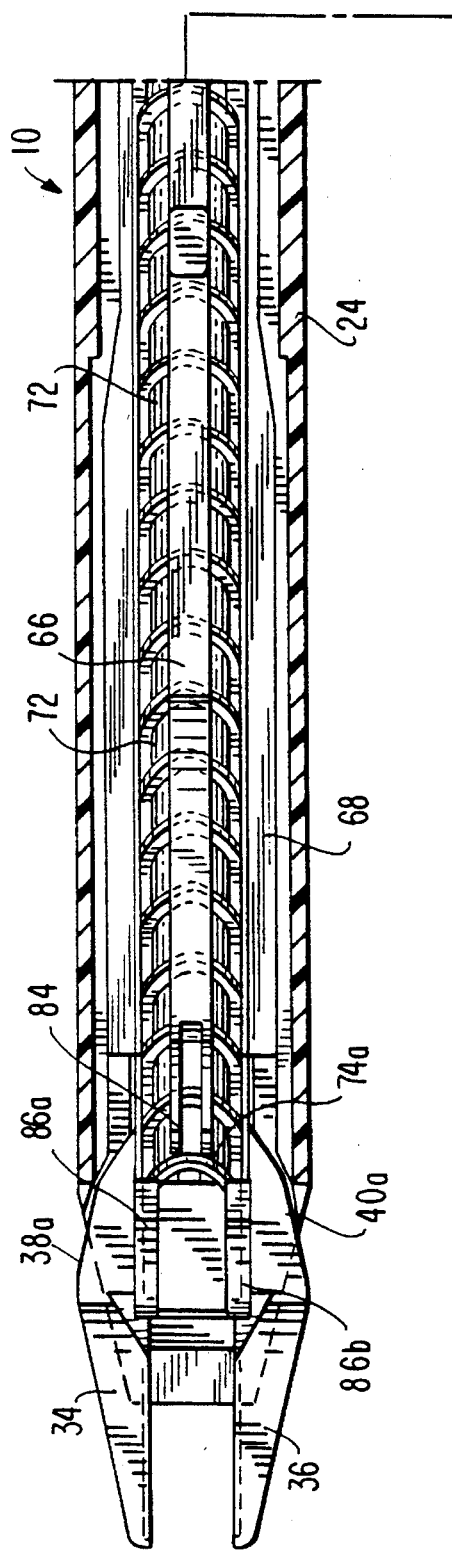
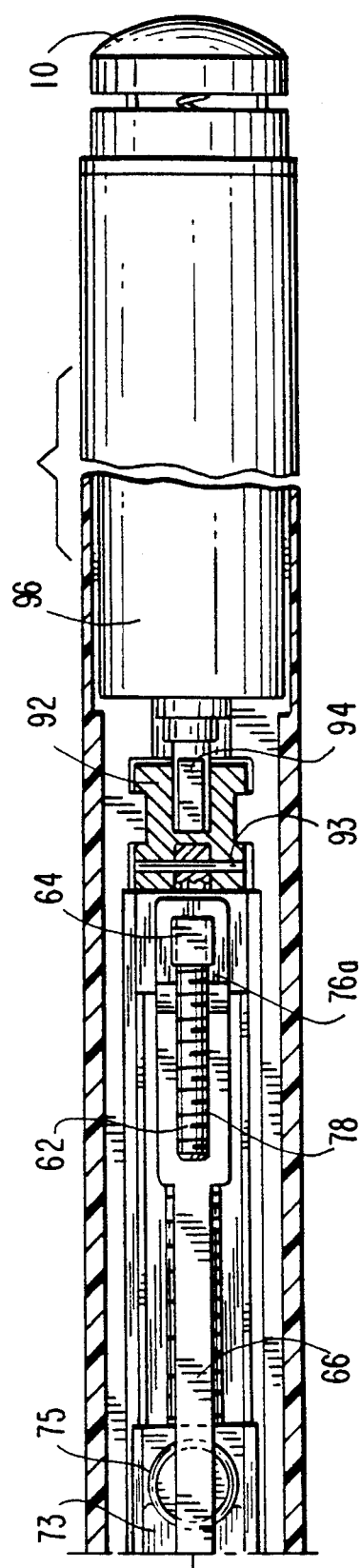
FIG. 6

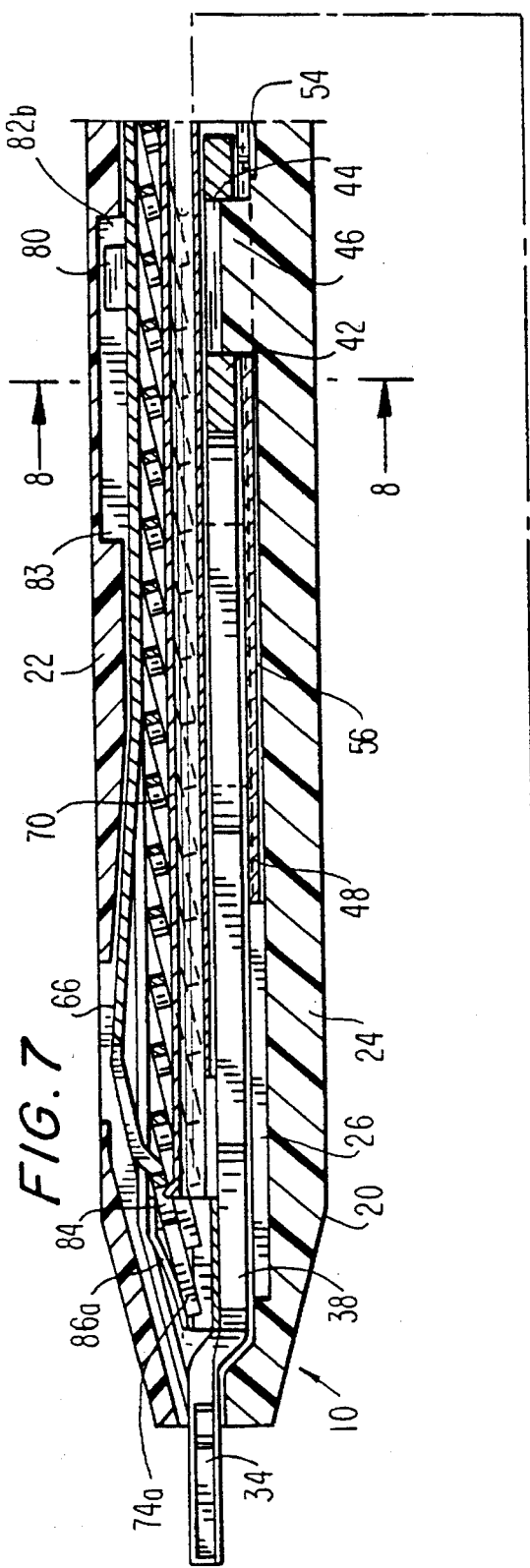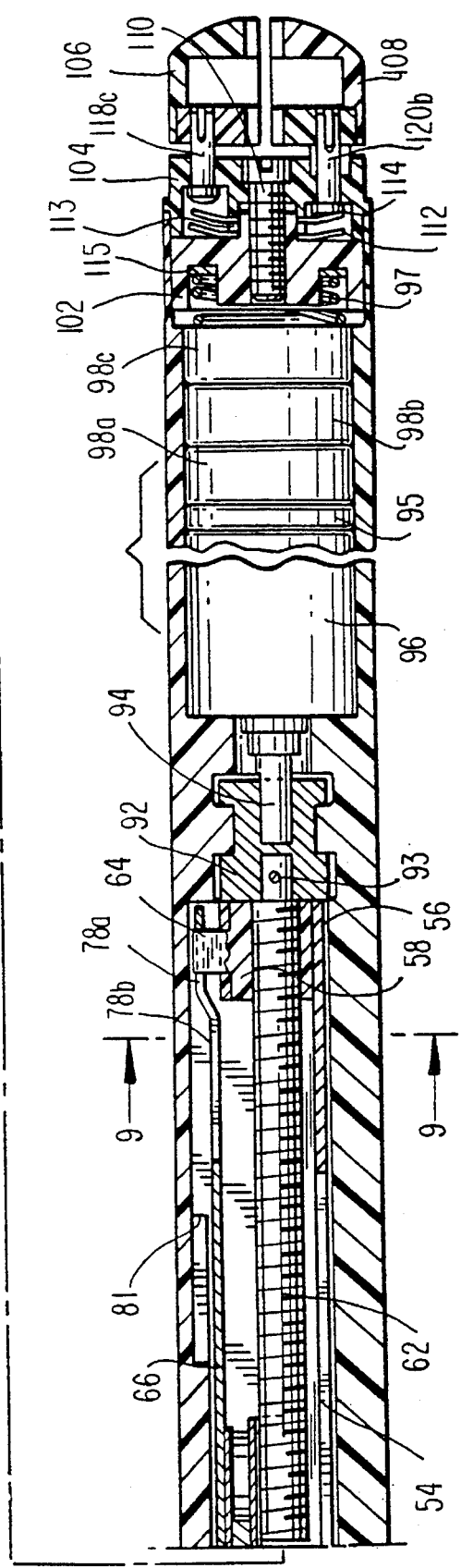

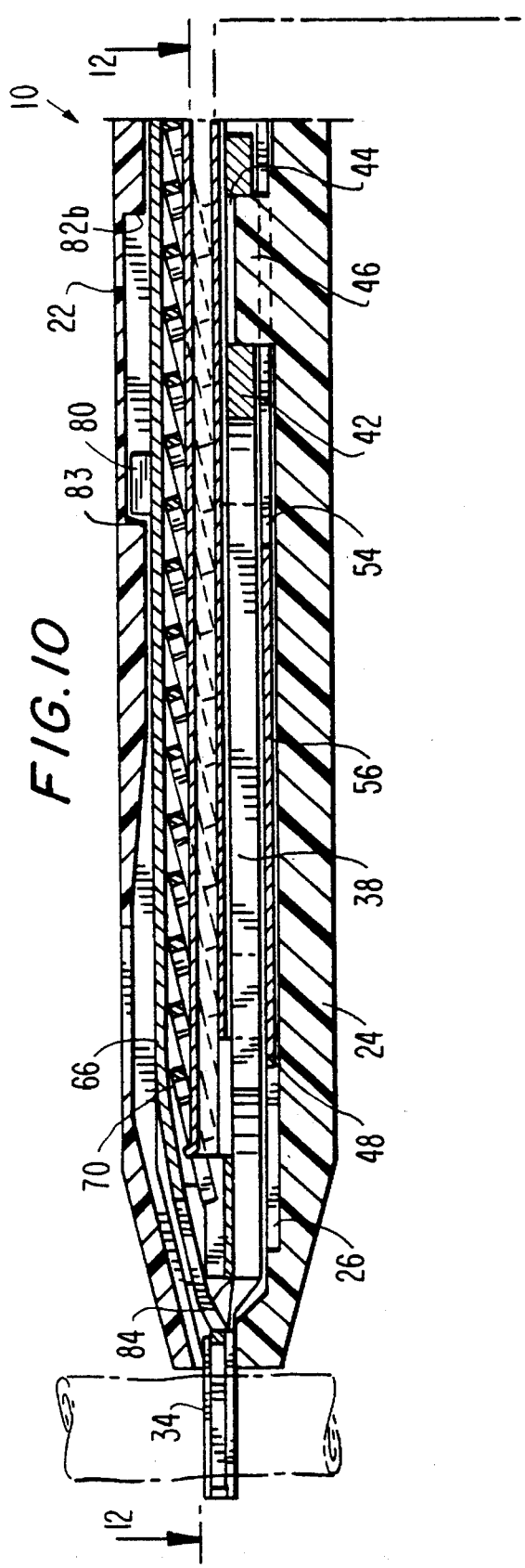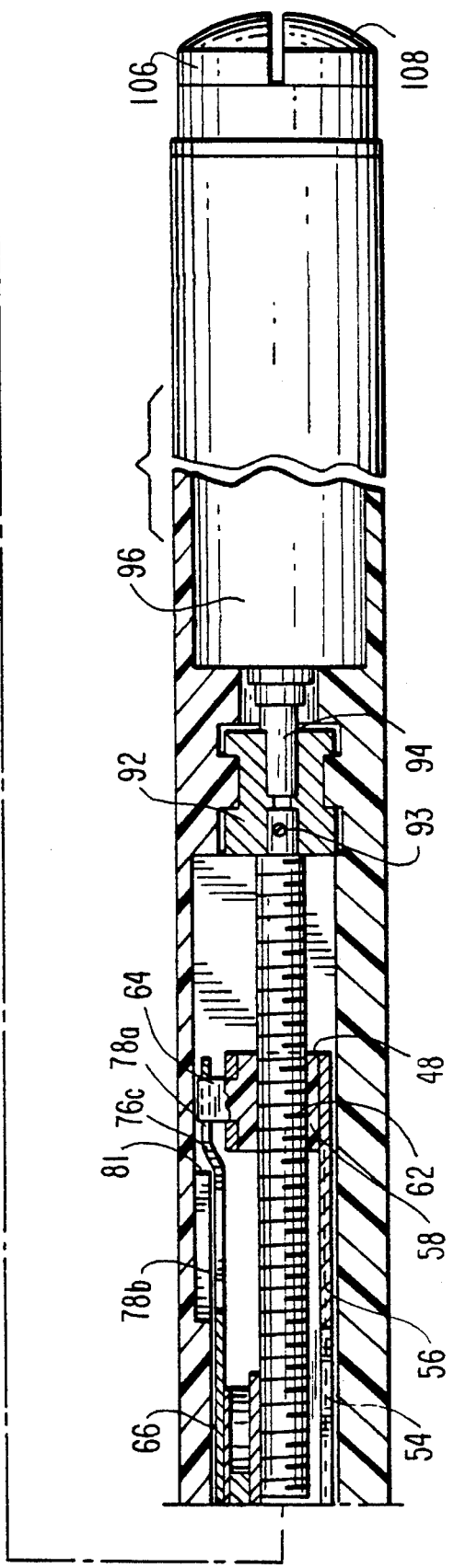
FIG. 10

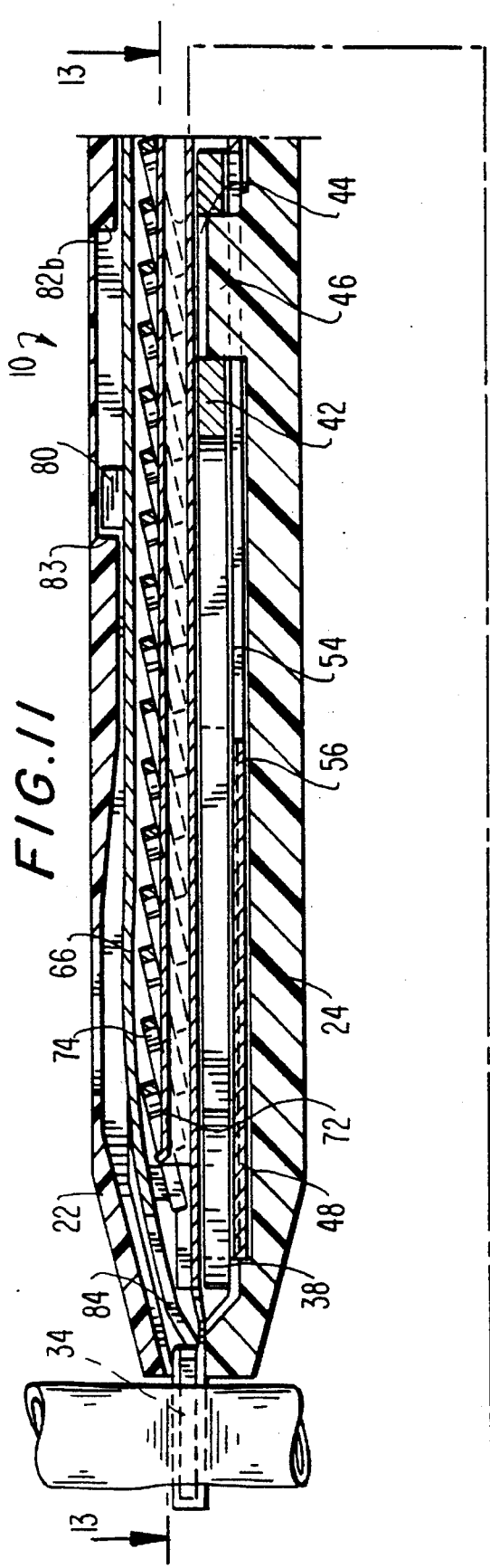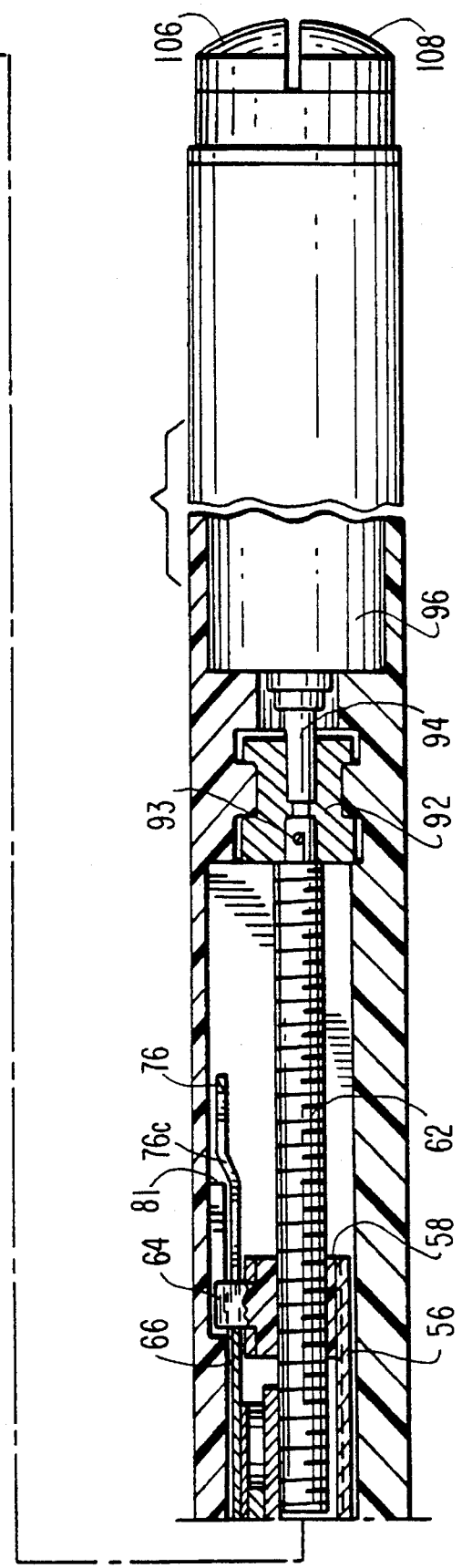
FIG.11

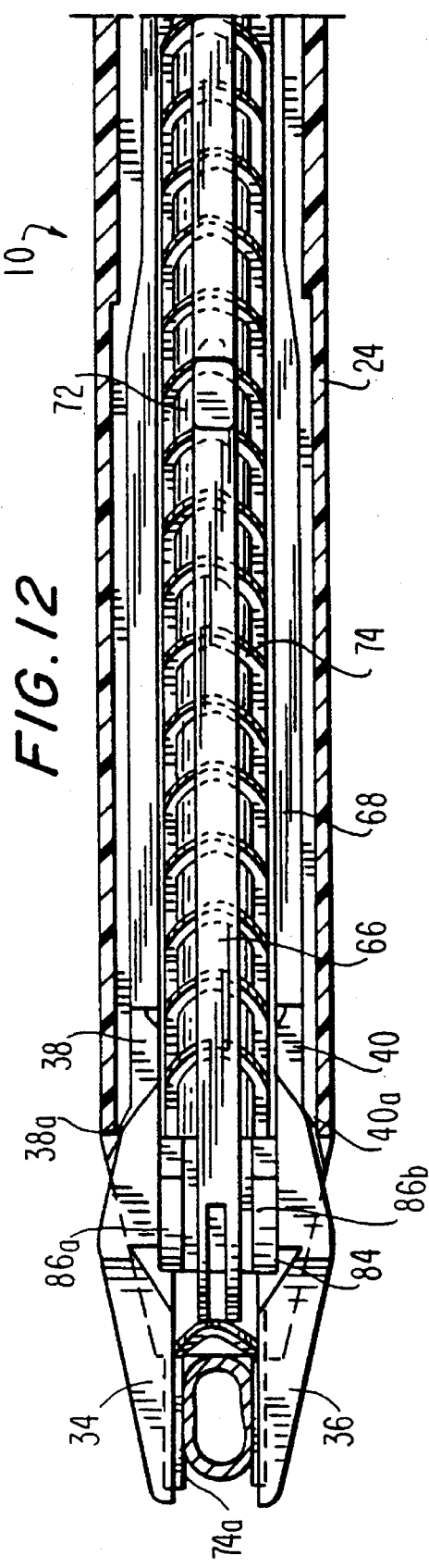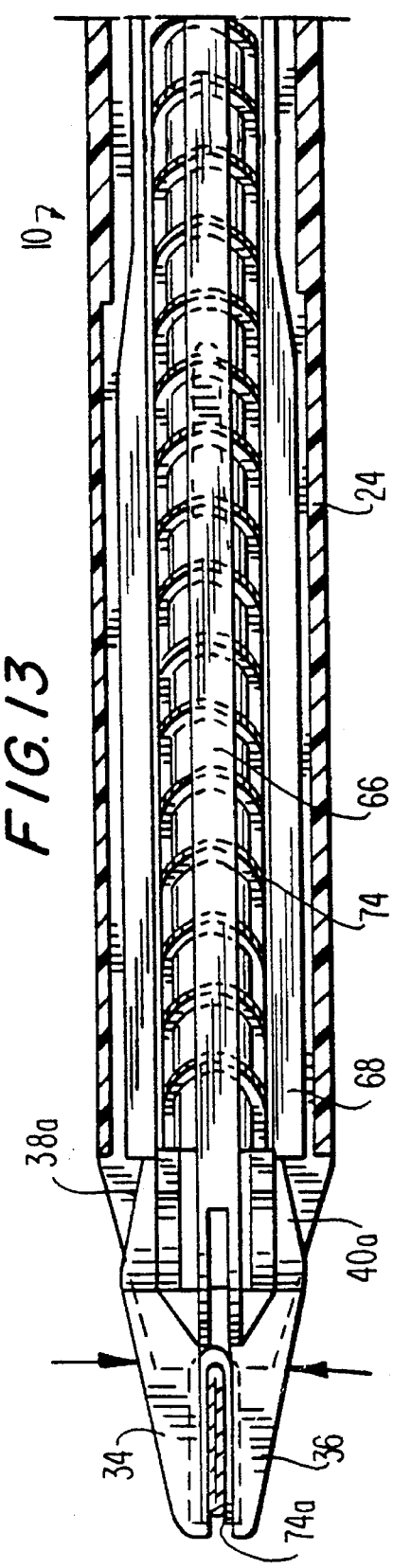

SELF-CONTAINED POWERED SURGICAL APPARATUS

BACKGROUND OF THE INVENTION

1. Field of the Invention

This invention relates to a serf-contained powered surgical apparatus for applying surgical clips to body tissue.

2. Description of Related Art

In laparoscopic and endoscopic surgical procedures, a small incision is made in the patient's body to provide access for a tube or cannula device. Once extended into the patient's body, the cannula allows insertion of various surgical instruments for acting on organs, blood vessels, ducts, or body tissue far removed from the incision. In general, an instrument utilized during an endoscopic procedure has an elongated body with a tool assembly associated with the distal end thereof and an actuation assembly at the proximal end thereof for controlling the operation of the tool assembly from a location remote from the surgical site. With the advent of laparoscopic surgery, the need for a suitable endoscopic hemostatic clip applier became clearly defined. Hemostatic clips are generally applied to blood vessels or ducts to prevent the flow of body fluids therethrough.

One example of a clip applier which is used in laparoscopic surgery is described in U.S Pat. No. 5,084,057. This instrument includes a mechanism for advancing a plurality of surgical clips towards a pair of distal jaw members. In operation, as each clip is dispensed from the apparatus, the clip advancement mechanism becomes positioned proximal to the distal-most clip in preparation for its advancement into the jaws. At a desired time, the user of the instrument manually releases the clip advancement structure to feed the distal-most clip into the jaw members. Thereupon, through actuation of handle structure, the jaw members are closed to advantageously crimp the clip.

Surgeons have also recognized the benefit of surgical instruments that are actuable with only a limited degree of physical force. Self-powered surgical instruments have been provided to serve these needs and include both gas powered surgical instruments as described, for example, in U.S. Pat. Nos. 3,815,476 and 3,837,555, and electrically powered surgical instruments as described, for example, in U.S. Pat. Nos. 4,635,638 and 5,258,007. A powered clip applying tool for use in laparoscopic surgery is described in European Patent Application 0 552 050. In general, prior art electrically powered instruments are driven by external power sources. Often, these instruments are connected to the external power sources by conductive cables. During a surgical procedure, cables can become entangled however, thereby complicating the operation.

It would be beneficial to provide a serf-contained powered surgical apparatus for applying hemostatic clips to body tissue. Such a device should be compact, lightweight, and easy to manufacture. Currently, surgical instruments are designed for use in either open, i.e. invasive procedures or endoscopic/laparoscopic procedures. As noted above, endoscopic instruments require elongated bodies to access remote surgical sites. Generally, conventional surgical instruments are not constructed in this manner. It would be advantageous to provide a powered clip applicator which can be readily adapted for use in endoscopic or laparoscopic procedures as well as conventional surgical procedures.

SUMMARY OF THE INVENTION

The subject invention is directed to a self-contained powered surgical apparatus for applying surgical clips to body tissue. The apparatus comprises an elongate body defining a longitudinal axis and housing a plurality of surgical clips. A jaw assembly is operatively associated with a distal end portion of the elongate body and is actuable to move between an open position and a closed position. A motor assembly and power source to energize the motor assembly are disposed within the elongate body. A clip pusher is configured to individually advance surgical clips into the jaw assembly. An elongate actuation mechanism is driven by the motor assembly to drive the clip pusher and actuate the jaw assembly. An actuator is positioned on the elongate body to selectively control the motor assembly.

The jaw assembly preferably includes first and second cooperating jaw members which depend from respective first and second opposed cantilevered camming beams, and the actuation mechanism preferably includes an actuation channel having opposed upstanding camming walls for engaging the first and second opposed camming beams to actuate the jaw assembly.

Preferably, the clip pusher has an elongate slot formed therein and the actuation channel includes an upstanding flange for slidably engaging the slot. The slot includes a proximal section configured to inhibit relative movement of the clip pusher and actuation channel and a distal section configured to accommodate such movement. Correspondingly, the flange includes an upper portion configured to inhibit relative movement of the clip pusher and actuation channel and a lower portion configured to facilitate such movement.

The actuation channel preferably includes a proximal engagement block having a threaded bore extending therethrough for threadably engaging an axial drive screw. In use, rotation of the drive screw will cause corresponding longitudinal translation of the actuation channel. More particularly, axial rotation of the drive screw in a first direction will cause the actuation channel to translate in a distal direction while axial rotation in a second direction will cause the actuation channel to translate in a proximal direction. The apparatus may include a first motor control button to effect distal movement of the actuation channel and a second motor control button to effect proximal translation of the actuation channel.

In one embodiment of the subject invention, the powered surgical apparatus includes an elongate shaft configured to engage with a proximal end of the main instrument body to facilitate utilization of the apparatus during an endoscopic procedure. Preferably, the extension shaft includes means for interacting with the actuator at the proximal end of the main instrument body to operate the apparatus from a location remote from the surgical site.

Further features of the powered surgical apparatus of the subject invention will become more readily apparent to those skilled in the art from the following detailed description of the preferred embodiments of the invention taken in conjunction with the drawings.

BRIEF DESCRIPTION OF THE DRAWINGS

So that one skilled in the art to which the subject invention appertains will better understand how to make and use the invention, preferred embodiments of the powered surgical apparatus will be described hereinbelow with reference to the drawings wherein:

FIGS. 2A and 2B illustrate rigid and flexible elongate extension shafts, respectively, depicting the powered clip applier of FIG. 1 in use during a laparoscopic procedure;

FIG. 6 is a cross-sectional view taken along line 6—6 of FIG. 1 illustrating the internal components of the powered clip applier of the subject invention;

FIG. 7 is a side elevational view in cross-section illustrating the relative position of the internal components of the powered clip applier of the subject invention prior to actuation;

FIG. 10 is a side educational view in cross-section illustrating the relative position of the internal components of the powered clip applier of the subject invention during a clip applying operation;

FIG. 11 is a side elevational view in cross-section illustrating the relative position of the internal components of the powered clip applier of the subject invention at the completion of a clip applying operation;

FIG. 12 is a top plan view in cross-section taken along line 12—12 of FIG. 10 illustrating the jaw assembly prior to closure; and FIG. 13 is a top plan view in cross-section taken along line 13—13 of FIG. 11 illustrating the jaw assembly in a closed position.

DETAILED DESCRIPTION OF THE PREFERRED EMBODIMENT

Figure 1:
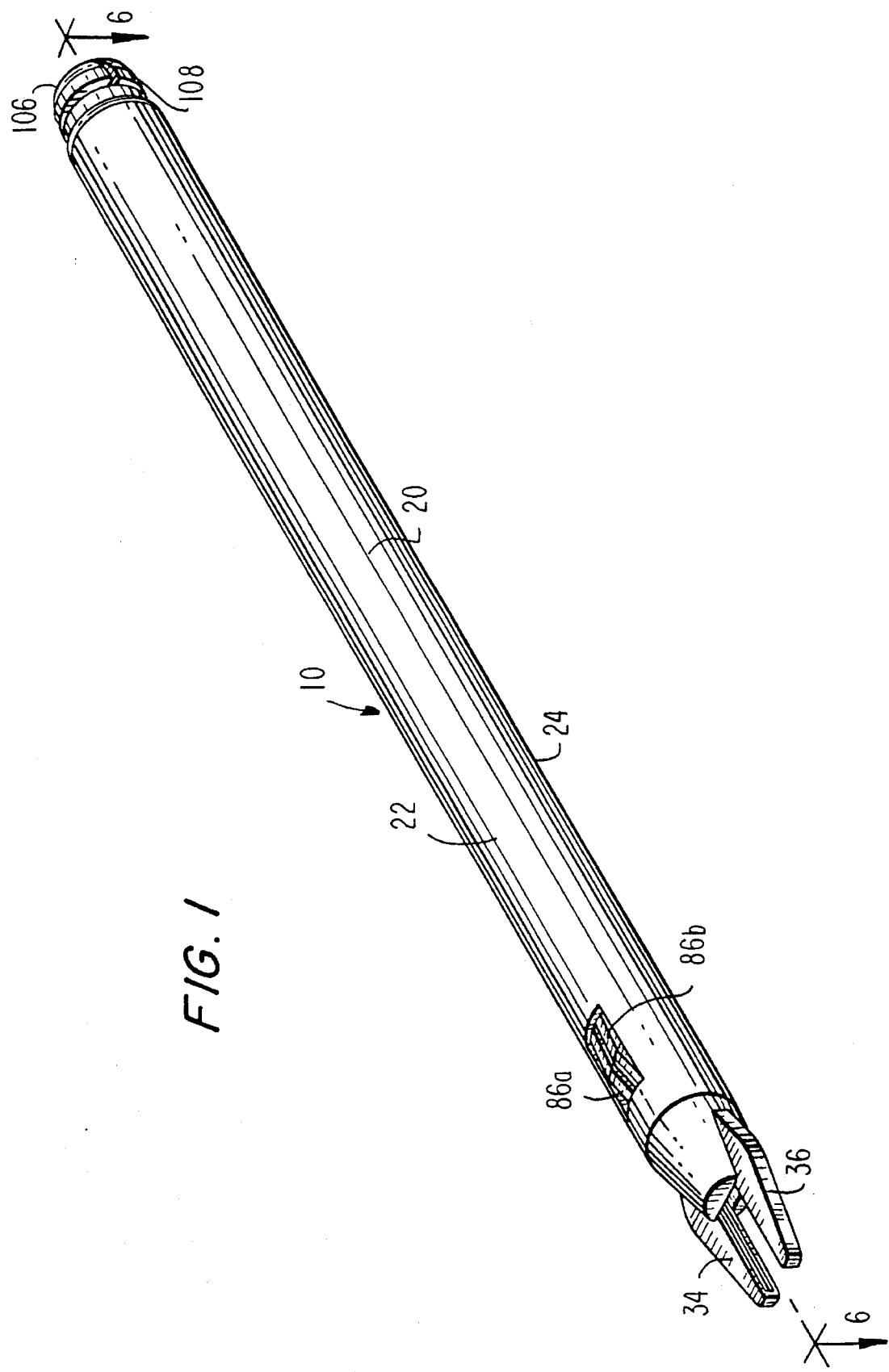
FIG. 1 is a perspective view of a powered clip applier constructed in accordance with a preferred embodiment of the subject invention.

In the drawings and in the description which follows, the term "proximal", as is traditional, will refer to the end of the apparatus which is closest to the operator, while the term "distal" will refer to the end of the apparatus which is furthest from the operator.

The present invention shall be discussed in terms of both conventional and endoscopic procedures and apparatus. However, use herein of terms such as "encloseopic", "endoscopically", and "endoscopic portion", among others, should not be construed to limit the present invention to an apparatus for use only in conjunction with an endoscopic tube. To the contrary, it is believed that the present invention may find use in procedures wherein access is limited to a small incision including but not limited to arthroscopic and/or laparoscopic procedures.

Referring now to the drawings wherein like reference numerals identify similar structural elements of the subject invention, there is illustrated in FIG. 1 a self-contained powered surgical clip applier constructed in accordance with a preferred embodiment of the subject invention and designated generally by reference numeral 10.

Figure 2A:
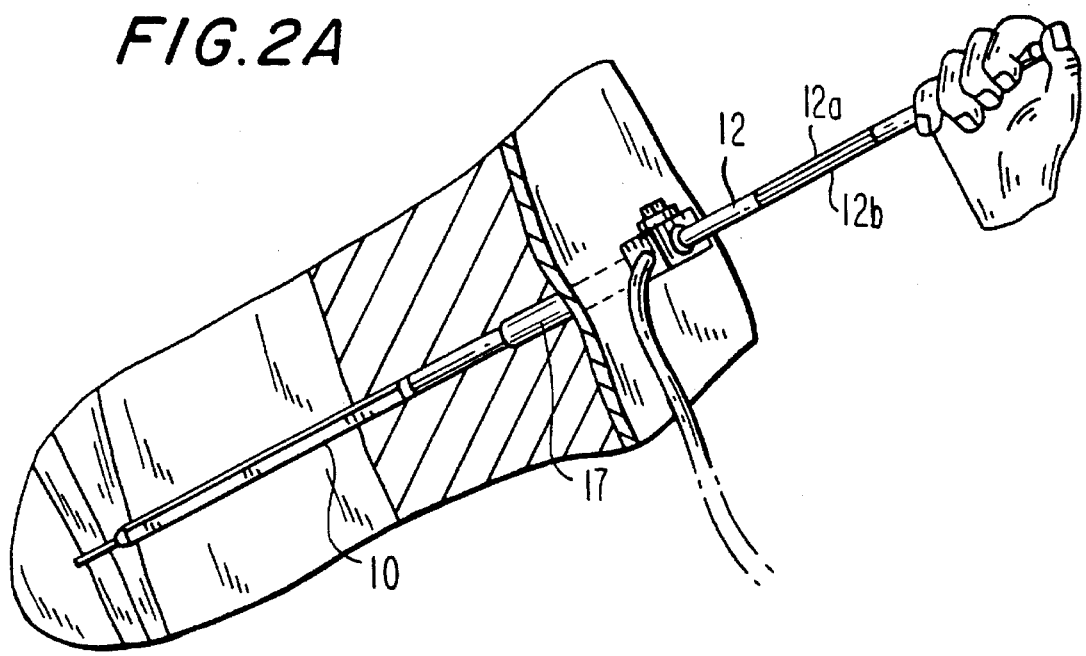

Referring to FIG. 1, powered surgical apparatus 10 is configured for use as a hand-held device for applying hemostatic clips to tubular vessels, ducts, and body tissue during conventional invasive surgical procedures. By way of example only, surgical apparatus 10 may have a length measuring from about 4.0 inches to about 9.0 inches, and an outer diameter of about 0.35 inches to about 0.55 inches. Preferably, surgical apparatus 10 has an operative length of 8.5 inches and a diameter of about 0.472 inches. Clearly, other dimensions are contemplated. In one embodiment of the subject invention, surgical apparatus 10 is also adapted for use in endoscopic procedures through remote actuation from a location outside the patient's body, as shown in FIGS. 2A and 2B. This is achieved by providing an elongated extension shaft 12 which attaches to the proximal end of surgical apparatus 10 by commonly known connective methods such as a snap fit. Extension shaft 12 is preferably dimensioned and configured for insertion through a cannula or trocar device and has a length measuring from about 8.0 inches to about 12.0 inches. A flexible shaft 12' or rigid shaft 12 can be utilized.

Figure 3:
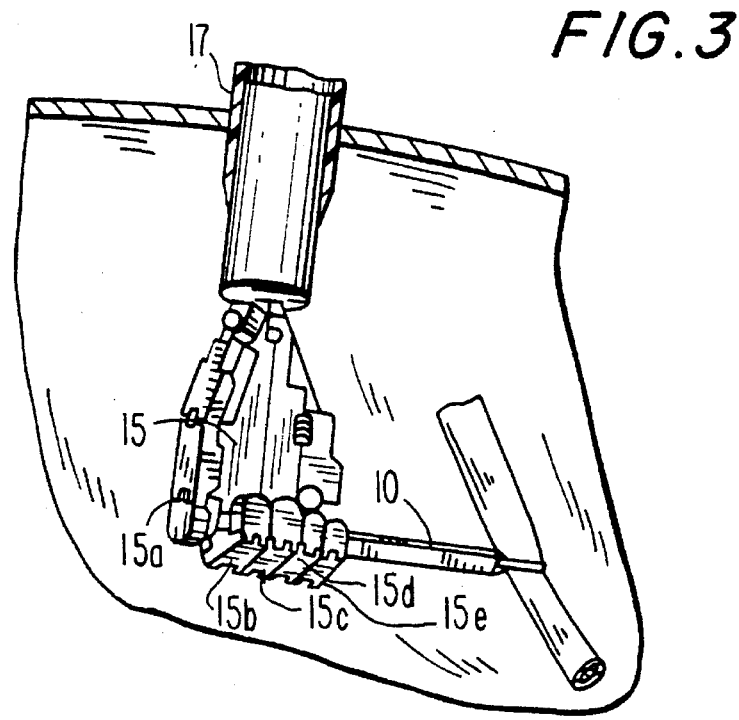
FIG. 3 is an illustration depicting a mechanical hand operating the powered clip applier of FIG. 1 during a laparoscopic procedure.

Referring to FIG. 3, in another preferred embodiment of the subject invention, surgical apparatus 10 is intended to be operated by a mechanical hand 15 which is configured to extend through trocar device 17 during a laparoscopic surgical procedure. Mechanical hand 15 includes four articulated fingers 15a–15d and an opposable thumb 15e which are hinged together to enable relative movement between a constricted position wherein the forehand and fingers are drawn together into a narrowed formation to facilitate their extension through trocar 17 and a relaxed position wherein the forehand and fingers are deployed into a spread position to perform dexterous tasks such as operating surgical apparatus 10 by actuating a switch provided on the apparatus.

Figure 4:
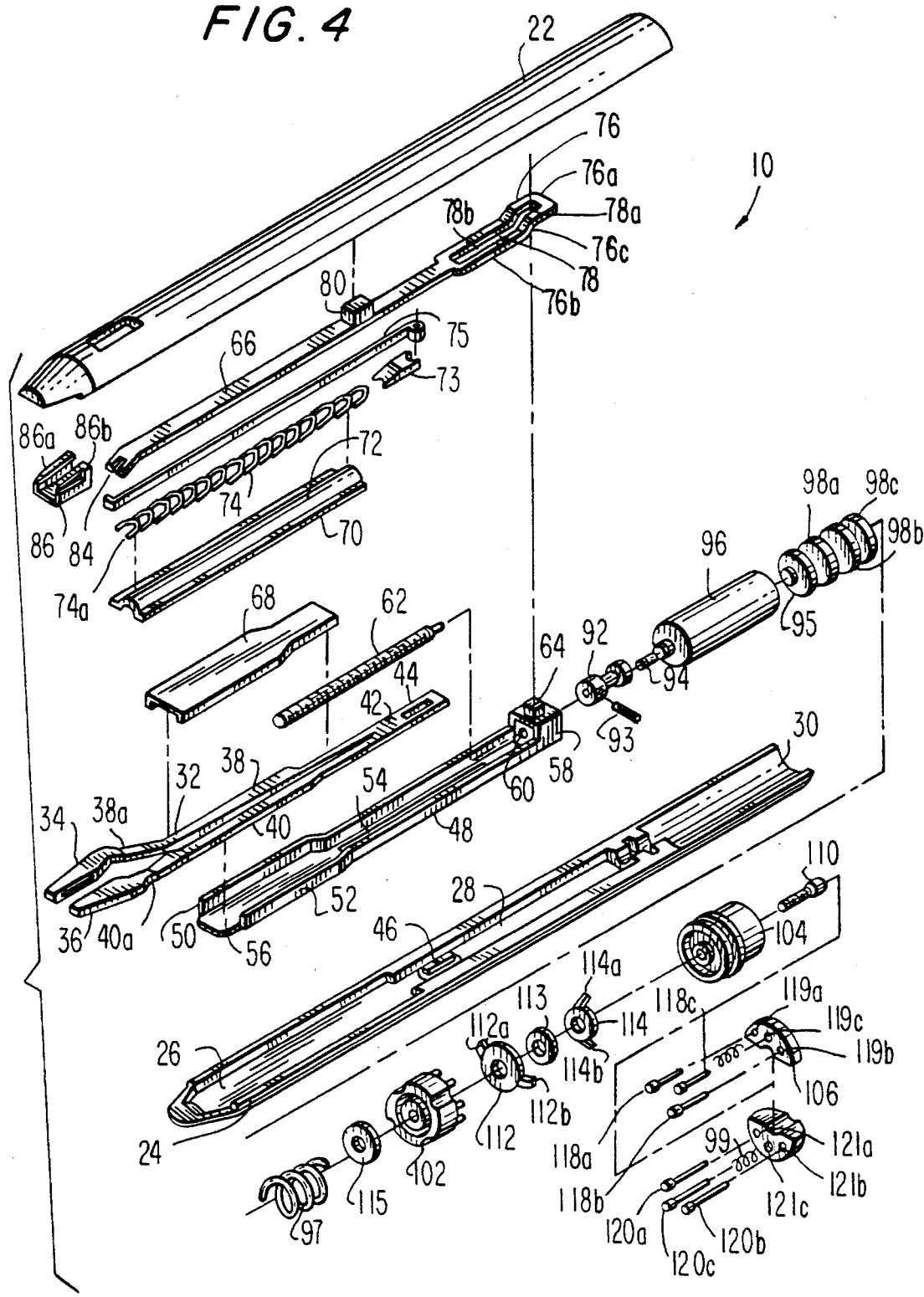
FIG. 4 is an exploded perspective view of the powered clip applier of FIG. 1.

Referring to FIG. 4, surgical apparatus 10 includes an elongate body 20 including complimentary body sections 22 and 24 which define a series of internal chambers for housing and supporting various mechanical components of apparatus 10 as well as a plurality of hemostatic clips for application to body tissue. The internal chambers defined within body sections 22 and 24 include distal chamber 26, medial chamber 28, and proximal chamber 30.

The internal components housed within body sections 22 and 24 of surgical apparatus 10 include a jaw assembly 32 having a pair of opposed clip forming jaws 34 and 36 which depend from cantilevered beams 38 and 40 respectively. Beams 38 and 40 define angled camming surfaces 38a and 40a respectively and extend from a proximal mounting portion 42. An aperture 44 is defined in proximal mounting portion 42 for receiving and engaging a projection 46 formed within medial chamber 28. This engagement prevents longitudinal movement of jaw assembly 32 with respect to body section 24.

A camming channel 48 is provided for interacting with jaw assembly 32 to move jaws 34 and 36 into a closed position to compress and deform a hemostatic clip disposed therebetween (see generally FIG. 13). Camming channel 48 includes opposed upstanding camming walls 50 and 52 for engaging the angled camming surfaces 38a and 40a of beams 38 and 40 during a clip applying operation. More particularly, as camming channel 48 is driven in a distal direction, camming walls 50 and 52 cause the opposed jaws 34 and 36 to approximate.

An elongated slot 54 is formed in the base 56 of camming channel 48 to accommodate projection 46 as camming channel 48 translates with respect thereto. A drive block 58 is provided at the proximal end of camming channel 48 and includes a threaded bore 60 for receiving an axial drive screw 62. An upstanding engagement flange 64 extends from drive block 58 for interacting with an elongate clip pusher 66. The interaction between the engagement flange 64 of camming channel 48 and the elongate clip pusher 66 will be discussed in detail below.

Figure 8:
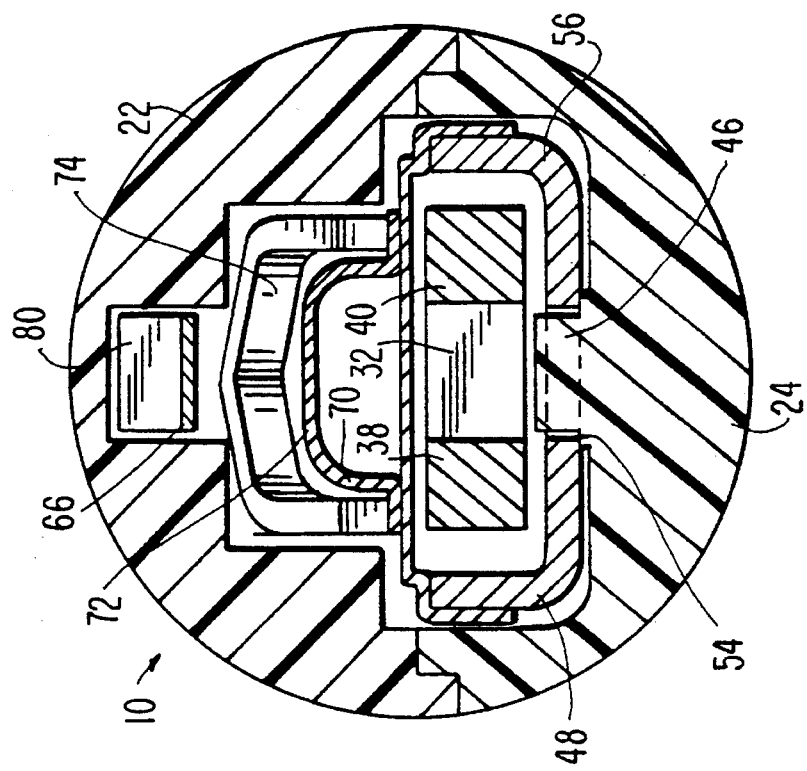
FIG. 8 is a cross-sectional view taken along line 8—8 of FIG. 7 illustrating the camming portion of the actuation channel.

A channel cover 68 is provided for enclosing a portion of jaw assembly 32 within camming channel 48. A clip support plate 70 is disposed adjacent channel cover 68 and includes an elongate rib 72 having an arcuate cross-sectional configuration upon which a plurality of hemostatic clips 74 are seated (see FIG. 8). Clips 74 are disposed in a train and are shown oriented on a 15° angle. The clip train is biased in a distal direction by a clip advancer 73. A constant force spring 75 is provided to supply the biasing force to clip advancer 73.

Figure 9:
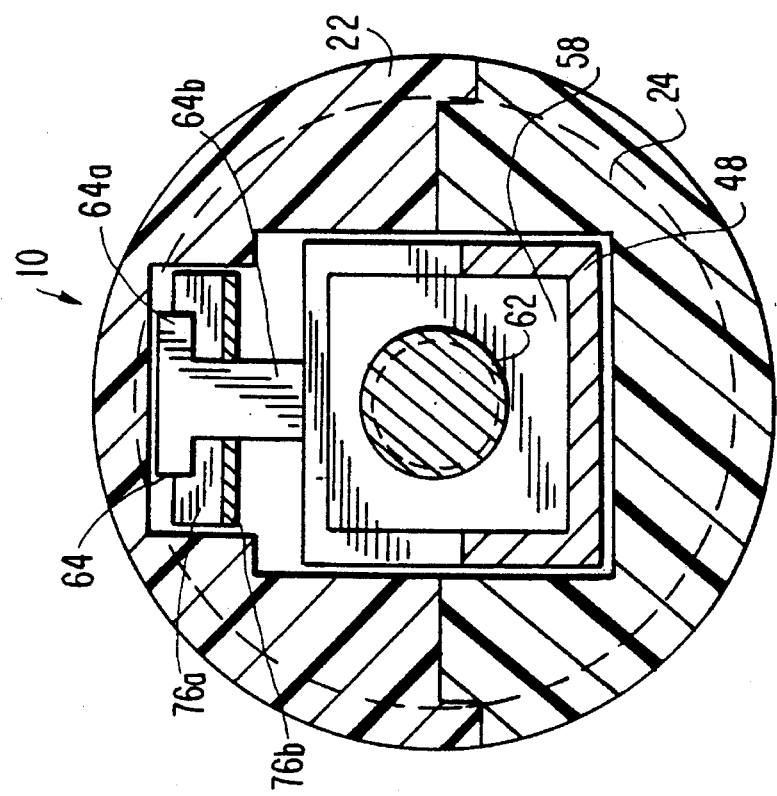
FIG. 9 is a cross-sectional view taken along line 9—9 of FIG. 7 illustrating the driving portion of the actuation channel.

Clip pusher 66 is provided for advancing the distal-most clip 74a into the opposed jaws 34 and 36 of jaw assembly 32 during a clip applying operation. Clip pusher 66 includes a stepped proximal portion 76 defining upper and lower sections 76a and 76b. An elongated engagement slot 78 extends through proximal portion 76 and defines a proximal section 78a and a distal section 78b. Proximal section 78a is wider than distal section 78b and is adapted to facilitate frictional engagement of a portion of flange 64 of channel 48 during the clip advancement stage of a clip applying operation. More specifically, flange 64 includes a substantially rectangular upper portion 64a for frictionally engaging proximal section 78a of slot 78, and a stepped lower portion 64b configured to translate through the distal section 78b of slot 78 during the jaw closing stage of a clip applying operation (see FIG. 9). An upstanding stop block 80 extends from the medial portion of clip pusher 66 to interact with a kicker spring 83 disposed within body section 22, as best seen in FIG. 7. Clip pusher 66 further includes a downturned clip engaging portion 84 at the distal end thereof for contacting the bail portion of the distal-most clip 74a. A clip biasing spring 86 is disposed within the distal portion of body section 22 which includes spring legs 86a and 86b for directing the distal-most clip 74a into jaws 34 and 36 of jaw assembly 32 as the clip is advanced distally by clip pusher 66.

With continued reference to FIG. 4, the proximal end of axial drive screw 62 is fastened to a hub member 92 by a retaining pin 93. Hub member 92 transfers torque from the drive shaft 94 of motor assembly 96 to drive screw 62 during a clip applying operation. Motor assembly 96 is housed within the proximal chamber 30 of body 20 and is powered by a plurality of internal power cells 98a–98c. The power cells may be rechargeable such as nickel-cadmium type batteries, standard alkaline type batteries, or lithium batteries, and are preferably replaceable. Power cells 98a–98c are biased in a distal direction toward transfer plate 95 by a coiled compression spring 97.

Surgical apparatus 10 further comprises a switching assembly 100 for selectively controlling the operation of motor assembly 96. Switching assembly 100 includes distal and proximal switch housings 102 and 104, and right and left actuation buttons 106 and 108. A plurality of coiled springs 99 bias actuation buttons 106 and 108 in a proximal direction. Switch housings 102 and 104 are mounted to one another and fastened to the proximal end of surgical apparatus 10 by a threaded connector 110, and are operatively separated from one another by a distal contact plate 112, an insulating ring 113, and a proximal contact plate 114. A proximal contact ring 115 is disposed between proximal switch housing 102 and compression spring 97. Distal contact plate 112 includes a pair of opposed upturned contact tabs 112a and 112b, and proximal contact plate 114 includes a pair of opposed upturned contact tabs 114a and 114b which are positioned approximately 60° out of phase with tabs 112a and 112b.

As illustrated in FIG. 4, each actuation button of switching assembly 100 has associated therewith three contact pins, two of which interact with contact plates 112 and 114. In particular, actuation button 106 includes two long pins 118a and 118b, and one short pin 118c. Short pin 118c is seated within a central reception port 119c, while long pins 118a and 118b are seated within lateral reception ports 119a and 119b. Long pin 118a and short pin 118c are positioned to selectively engage contact tabs 112a and 114a respectively, while long pin 118b remains free from electrical contact with either plate. Similarly, actuation button 108 includes long pins 120a and 120b, and short pin 120c. Short pin 120c is seated within a central reception port 121c, while long pins 120a and 120b are seated within lateral reception ports 121a and 121b. Long pin 120b and short pin 120c are positioned to selectively engage contact tabs 112b and 114b respectively, while long pin 118b remains free from electrical contact within either plate.

Figure 5:
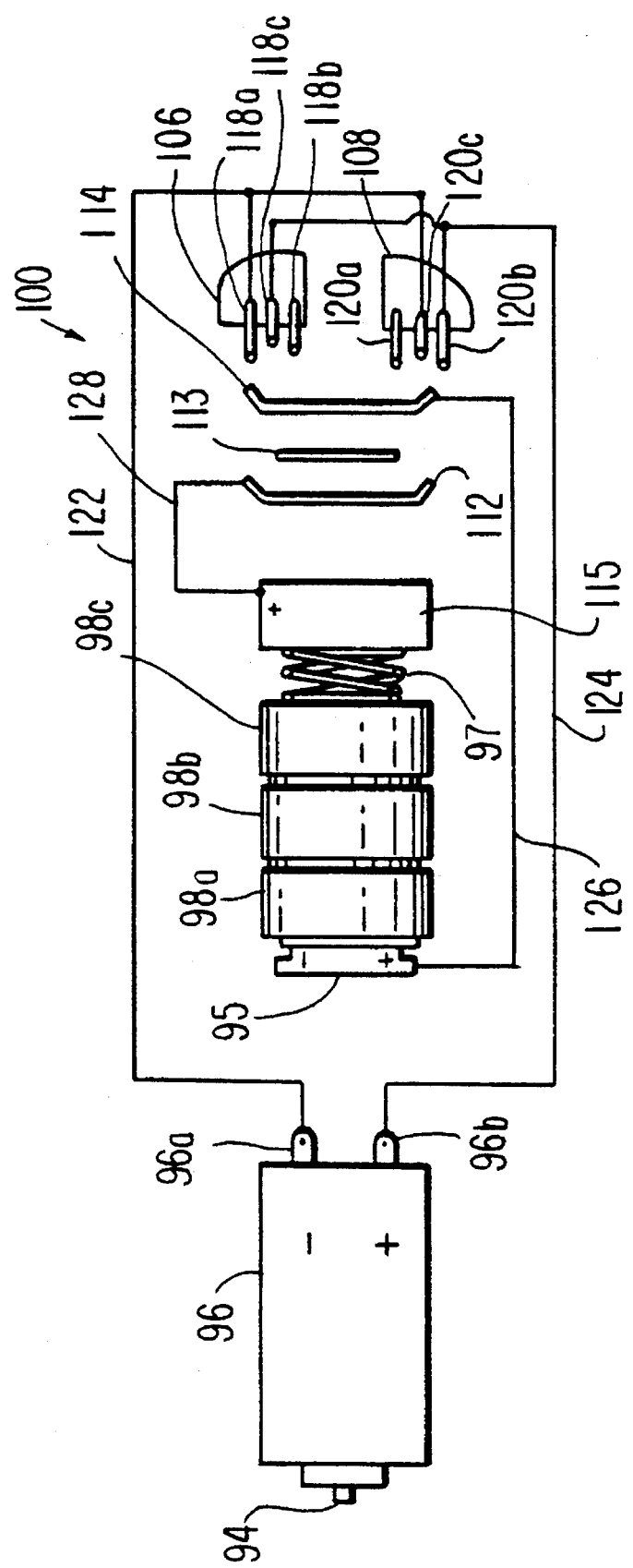
FIG. 5 is a schematic representation of the switching mechanism for controlling the operation of the motor assembly of the subject invention.

The wiring configuration of switching assembly 100 is illustrated in FIG. 5 and includes a motor line 122 which interconnects the positive terminal 96b of motor assembly 96 to contact pins 118a and 120c, and a motor line 124 which interconnects the negative terminal 96a of motor assembly 96 to contact pins 118c and 120b. In addition, a transmission line 126 extends between transfer plate 95 and contact plate 114, and a transmission line 128 interconnects contact plate 112 and proximal contact ring 115.

In use, when actuation button 106 is depressed, long pin 118a contacts tab 112a of contact plate 112 and short pin 118c contacts tab 114a of contact plate 114. Thus the positive terminals of power cells 98a–98c are connected to the negative terminal 96a of motor assembly 96 and the negative terminals of power cells 98a–98c are connected to the positive terminal 96b of motor assembly 96, causing drive shaft 94 to rotate in a counter-clockwise direction. When actuation button 108 is depressed, long pin 120b contacts tab 112b of contact plate 112 and short pin 120c contacts tab 114b of contact plate 114. Thus, the positive terminals of power cells 98a–98c are connected to the positive terminal 96b of motor assembly 96 and the negative terminals of power cells 98a–98c are connected to the negative terminal 96a of motor assembly 96, causing drive shaft 94 to rotate in a clockwise direction.

As discussed briefly hereinabove, surgical apparatus 10 can also be designed for insertion through a trocar or cannula device to apply hemostatic clips to body tissue located within a body cavity while being actuable remote from the surgical site. Referring to FIGS. 2A or 2B, to facilitate such use, elongate extension shaft 12 or 12' is attached to the proximal end of surgical apparatus 10. The shaft includes elongate transmission members 12a and 12b (or 12a', 12b') for effectuating remote actuation of switching assembly 100. Transmission members 12a and 12b (or 12a', 12b') may comprise a pair of substantially rigid rods for transmitting a mechanical signal to actuation buttons 106 and 108, or, in the alternative, the transmission members may comprise transmission cables for directing an electrical signal to switching assembly 100. In either instance, the shaft would include two actuation buttons to respectively actuate buttons 106 and 108 and cause the rotation of drive screw 62 in opposed directions.

As noted above, surgical apparatus 10 can also be configured to be used in laparoscopic procedures without the extension shaft 12 by employing the mechanical hand illustrated in FIG. 3. Due to the single actuation features of the subject invention, e.g. push button actuation, the articulated fingers of mechanical hand 15 can be easily manipulated to operate the instrument and perform a surgical task.

Referring now to FIGS. 6–13, the operation of surgical apparatus 10 will be described. Prior to actuation, the distal portion 84 of clip pusher 66 is engaged behind the distalmost clip 74a and the opposed jaws 34 and 36 of jaw assembly 32 are disposed in an open position, as shown in FIG. 6, and camming channel 48 is disposed in the proximal position best seen in FIG. 7. At such a time, the upper portion 64a of engaging flange 64 is frictionally engaged in the proximal section of slot 78. Upon depressing actuation button 106, motor assembly 96 will be engaged and drive shaft 94 will rotate in a counter-clockwise direction. As a result, axial drive screw 62 will rotate causing camming channel 48 to translate in a distal direction within medial chamber 28. Also, clip pusher 66 will be driven in a distal direction due to the frictional engagement of flange 64, thereby urging the distal most clip 74a towards the opposed jaws 34 and 36 of jaw assembly 32.

Continued rotation of drive screw 62 will effect further distal translation of clip pusher 66 until stop block 80 abuts and compresses kicker spring 83. Simultaneously, the ramped area 76c defined between section 76a and 76b of clip pusher 66 is biased downward by transverse surface 81 until the upper portion 64a of flange 64 is disengaged from the proximal section 78a of slot 78. At such a time, kicker spring 83 biased clip pusher 66 in a proximal direction, urging the distal end thereof out of the opposed jaws 34 and 36 of jaw assembly 32, and however, distal movement of camming channel 48 continues. At this point a clip has been fed into the jaws 34, 36 but the jaws are not yet cammed to their closed position. With flange 64 re-oriented in the distal section 78b of slot 78 as illustrated in FIG. 11, the continued distal translation of camming channel 48 is uninhibited.

Referring to FIG. 13, upon further distal movement of camming channel 48, the opposed upstanding camming walls 50 and 52 of camming channel 48 engage camming surfaces 38a, 40a to urge jaws 34 and 36 inwardly to compress and deform the hemostatic clip 74a disposed therebetween.

Following the clip applying operation, the user may depress actuation button 108 to cause motor assembly 96 to turn drive screw 62 in an opposite direction. As a result, drive member 62 will translate in a proximal direction initially drawing camming channel 48 proximally. Flange 64 will ride proximally in slot 78 of clip pusher 66. Upon engagement with proximal section 78a, the clip pusher 66 is pulled rearwardly as channel 48 moves rearwardly. The clip pusher 66 is drawn in a proximal direction until stop block 80 abuts a proximal stop surface 82b, at which time flange 64 moves up the ramp 76c on clip pusher 66 to engage proximal section 78a of engagement slot 78. Then, the user may release actuation button 108. At this time, both clip pusher 66 and camming channel 48 are in a proximalmost position (FIGS. 6 and 7). To apply another clip, actuation button 106 is depressed to drive the clip pusher 66 and channel 48 distally as described above.

Although the subject invention has been described with respect to preferred embodiments, it will be readily apparent to those having ordinary skill in the art to which it appertains that changes and modifications may be made thereto without departing from the spirit or scope of the subject invention as defined by the appended claims.

What is claimed is:

1. A self-contained powered surgical apparatus for applying surgical clips to body tissue comprising:
   a) an elongate body having an internal cavity formed therein, defining a longitudinal axis and housing a plurality of surgical clips;
   b) a jaw assembly supported at a distal end portion of the elongate body and including a pair of opposed cooperating jaw members actuable to move between an open position and a closed position with respect to the longitudinal axis of the body;
   c) an electric motor assembly mounted within the internal cavity of the elongate body;
   d) a clip pusher slidably supported in the elongate body adjacent the plurality of surgical clips and actuable to individually advance the surgical clips into the jaw assembly;
   e) an elongate actuation mechanism disposed within the elongate body, driven by the motor assembly, and mounted to translate longitudinally through the elongate body upon actuation of the motor assembly to drive the clip pusher and actuate the jaw assembly; and
   f) an electrical power source disposed within the internal cavity of the elongate body and electrically connected to the motor assembly for energizing the motor assembly to drive the actuation mechanism.

2. A powered surgical apparatus as recited in claim 1, wherein the opposed cooperating jaw members depend from respective first and second opposed cantilevered camming beams which are connected to one another at proximal ends thereof.

3. A powered surgical apparatus as recited in claim 2, wherein the actuation mechanism defines an actuation channel which includes opposed upstanding camming walls which engage the first and second opposed camming beams as the actuation mechanism translates with respect thereto to actuate the jaw assembly.

4. A powered surgical apparatus as recited in claim 1, wherein the clip pusher has an elongate slot formed therein and the actuation mechanism includes an actuation channel having an upstanding flange positioned adjacent a proximal end thereof for slidably engaging the slot.

5. A powered surgical apparatus as recited in claim 1, wherein the clip pusher is operatively connected to and advanced by the actuation mechanism.

6. A powered surgical apparatus as recited in claim 5, wherein the actuation mechanism includes an actuation channel and wherein upon actuation of the motor assembly the clip pusher and actuation channel initially move distally and subsequently the actuation channel moves distally and the clip pusher remains stationary.

7. A powered surgical apparatus as recited in claim 6, further comprising an axial drive screw connecting the actuation channel to the motor assembly.

8. A powered surgical apparatus as recited in claim 7, wherein the clip pusher includes a stop block which interacts with an abutment surface defined in the internal cavity of the elongate body for limiting distal movement of the clip pusher.

9. A powered surgical apparatus as recited in claim 4, wherein the elongate slot formed in the clip pusher includes a proximal section configured to inhibit relative movement of the clip pusher and actuation channel by frictionally retaining the upstanding flange and a distal section configured to accommodate relative movement of the clip pusher and the actuation channel by affording free movement of the upstanding flange therethrough.

10. A powered surgical apparatus as recited in claim 4, wherein the upstanding flange includes an enlarged upper portion configured to contact the periphery of the slot to inhibit relative movement of the clip pusher and actuation channel and a tapered lower portion configured to slide through the slot to facilitate relative movement of the clip pusher and actuation channel.

11. A powered surgical apparatus as recited in claim 1, wherein the actuation mechanism includes an axial drive screw driven by the motor assembly.

12. A powered surgical apparatus as recited in claim 11, wherein the actuation mechanism includes an actuation channel and the axial drive screw includes a mounting flange to engage the actuation channel.

13. A powered surgical apparatus as recited in claim 12, wherein the actuation channel includes an upstanding engagement structure positioned adjacent a proximal end thereof and having a threaded bore extending therethrough for threadably engaging the axial drive screw.

14. A powered surgical apparatus as recited in claim 1, wherein the elongate body includes a first actuator button electrically connected to the motor assembly for effecting distal translation of the actuation mechanism and a second actuator button electrically connected to the motor assembly for effecting proximal translation of the actuation mechanism.

15. A powered surgical apparatus as recited in claim 14, further comprising an elongate extension shaft configured for engagement with a proximal end of the elongate body to facilitate utilization of the apparatus during an endoscopic surgical procedure.

16. A powered surgical apparatus as recited in claim 15, wherein the elongate extension shaft includes means connecting with the first and second actuator buttons to effectuate remote operation of the apparatus.

17. A powered surgical apparatus as recited in claim 16, wherein the means connecting with the first and second actuator buttons comprises a pair of elongate rod members mounted for longitudinal movement within the extension shaft.

18. A powered surgical apparatus as recited in claim 1, wherein the elongate body has a substantially uniform diameter.

19. A powered surgical apparatus as recited in claim 1, wherein the elongate body has an operative length of less than 10.0 inches.

20. A surgical apparatus as recited in claim 1, further comprising means positioned within the elongate body adjacent the surgical clips for biasing the surgical clips toward the distal end of the elongate body.

21. A self-contained powered surgical apparatus for applying surgical clips to body tissue comprising:

a) an elongate body having an internal cavity formed therein, defining a longitudinal axis, and housing a plurality of surgical clips;

b) a pair of jaws extending from a distal end portion of the elongate body, the jaws being relatively moveable between open and closed positions and supporting a surgical clip advanced therebetween;

c) clip advancing means movably supported within the elongate body adjacent the plurality of surgical clips for individually advancing the surgical clips into the pair of jaws;

d) jaw moving means disposed within the elongate body and mounted to translate relative to the jaws for moving the jaws between open and closed positions;

f) an electric motor assembly disposed within the internal cavity of the elongate body and operatively connected to the clip advancing means and the jaw moving means for translating the clip advancing means to feed a clip into the jaws and for actuating the jaw moving means to open and close the jaws;

g) control means positioned on the elongate body and electrically connected to the motor assembly for selectively actuating the motor assembly; and h) means disposed within the internal cavity of the elongate body and electrically connected to the motor assembly for energizing the motor assembly.

22. A surgical apparatus as recited in claim 21, wherein the pair of jaws depend from respective first and second opposed cantilevered camming beams which are connected to one another at proximal ends thereof.

23. A powered surgical apparatus as recited in claim 22, wherein the jaw moving means comprises an elongate actuation channel including opposed upstanding camming walls which engage the first and second opposed camming beams to actuate the jaws.

24. A powered surgical apparatus as recited in claim 23, further comprising an axial drive screw operatively connected to the motor assembly and engagable with the actuation channel to translate the actuation channel.

25. A powered surgical apparatus as recited in claim 24, wherein the actuation channel includes an upstanding engagement structure positioned adjacent the proximal end thereof and having a threaded bore extending therethrough for threadably engaging the axial drive screw.

26. A powered surgical apparatus as recited in claim 23, wherein the clip advancing means comprises an elongated clip pusher having an elongate slot formed therein adjacent a proximal end thereof and the actuation channel includes an upstanding flange adjacent a proximal end thereof for sequentially engaging the elongate slot.

27. A powered surgical apparatus as recited in claim 26, wherein the elongate body has a substantially uniform diameter and the motor assembly and control means are positioned on a proximal end portion of the elongate body.

28. A powered surgical apparatus for applying surgical clips to body tissue comprising:

a) an elongate main instrument body housing a plurality of surgical clips;

b) a jaw assembly supported at a distal end portion of the main instrument body and including a pair of relatively movable jaw members configured to support a surgical clip advanced therebetween and actuable to move between an open position and a closed position to apply the surgical clip advanced therebetween to body tissue;

c) a clip pusher slidably mounted in the main instrument body and actuable to individually advance the surgical clips into the jaw members of the jaw assembly;

d) an electric motor assembly disposed within the main instrument body and mechanically connected to the jaw assembly for actuating the jaw members; and e) an elongate extension shaft removably mounted to a proximal end portion of the main instrument body to increase the operative length of the apparatus to facilitate utilization of the main instrument body during an endoscopic surgical procedure.

29. A powered surgical apparatus as recited in claim 28, further comprising a control switch positioned at a proximal end of the main instrument body and electrically connected to the motor assembly for selectively controlling the motor assembly.

30. A powered surgical apparatus as recited in claim 29, wherein the elongate extension shaft includes control means for connecting with the control switch on the main instrument body to effectuate remote operation of the motor assembly.

31. A powered surgical apparatus as recited in claim 30, wherein the main instrument body has an operative length ranging from about 4.0 inches to about 9.0 inches, and the extension shaft has an operative length ranging from about 4.0 inches to about 10.0 inches.

32. A powered surgical apparatus as recited in claim 28, further comprising an electrical power source disposed within one of said main instrument body and said elongate extension shaft and electrically connected to the motor assembly for energizing the motor assembly.

33. A powered surgical apparatus as recited in claim 28, wherein the clip pusher is operatively connected to the motor assembly and the motor assembly is driven through the main instrument body thereby.

\* \* \* \* \*